United States Patent [19]

Baxter et al.

[11] 4,322,499
[45] Mar. 30, 1982

[54] ADRENOCORTICOTROPIN-LIPOTROPIN PRECURSOR GENE

[75] Inventors: John D. Baxter; James L. Roberts; Peter H. Seeburg; Howard M. Goodman, all of San Francisco, Calif.; John Shine, Curtin, Australia

[73] Assignee: The Regents of the University of California, Berkeley, Calif.

[21] Appl. No.: 972,430

[22] Filed: Dec. 22, 1978

[51] Int. Cl.³ .............................................. C12N 1/00
[52] U.S. Cl. ..................................... 435/317; 435/68; 435/91; 435/172; 435/253
[58] Field of Search ................ 435/172, 253, 317, 255

[56] References Cited

U.S. PATENT DOCUMENTS 4,237,224 12/1980 Cohen et al. .................... 435/183

OTHER PUBLICATIONS

Seebring et al., Nature, vol. 270, pp. 486–494, Dec. 8, 1977.
Guillemin, Science, vol. 202, pp. 390–402, Oct. 27, 1978.
Roberts et al., Proc. Natl. Acad. Sci. USA, vol. 74, pp. 4826–4830, Nov. 1977.
Maxam et al., Proc. Natl. Acad. Sci. USA, vol. 74, pp. 560–584, Feb. 1977.
Heyneker, et al., Nature, vol. 263, pp. 748–752, (1976).
Itakura et al., Science 198, pp. 1056–1063, (1977).
Jacob et al., J. Mol. Biol. 31, pp. 704–719, (1965).
Li et al, Proc. Nat. Acad. Sci, USA, vol. 73, pp. 1145–1148, (1976).
Benzer et al., PNAS 48, pp. 1114–1121, (1962).
Chang et al., Proc. Natl. Acad. Sci. USA, vol. 75, pp. 361–365, Jan. 1978.
Chang et al., Nature, vol. 275, pp. 617–624, Oct. 19, 1978.
Herrlich et al., Methods in Enzymology, vol. 61, pp. 654–669, 1974.
Mains et al., Proc. Natl. Acad. Sci., vol. 74, pp. 3014–3018, Jul. 1977.
Mercereau-Puijalon et al., Nature 275, pp. 505–510, (1978).
Polisky et al., Proc. Natl. Acad. Sci. USA, vol. 73, pp. 3900 (1976).
Roberts et al., Biochemistry 17, pp. 3609–3618, (1978).
Roberts et al., Proc. Natl. Acad. Sci. USA, vol. 74, pp. 5300–5304, Dec. 1977.
Roberts et al., Crit. Rev. Biochem. 4, pp. 123–164, (1976).
Sanger et al., Proc. Natl. Acad. Sci. USA, vol. 74, pp. 5463–5467, Dec. 1977.
Scheller et al., Science, vol. 196, pp. 177–180, Apr. 1977.
Ullrich et al., Science, vol. 196, pp. 1313–1319, Jun. 1977.
Villa-Komaroff, et al., Proc. Natl. Acad. Sci., vol. 75, pp. 3727–3731, (Aug. 1978).

Primary Examiner—Alvin E. Tanenholtz

[57] ABSTRACT

A technique suitable for cloning a cDNA having a base sequence coding for the ACTH/LPH precursor is disclosed. The invention is exemplified by the cloning of a cDNA fragment comprising a base sequence coding for the endorphin region. The fragment, hereinafter termed the endorphin gene cDNA sequence, was obtained from cultured mouse pituitary tumor cells known to produce the ACTH/LPH precursor protein.

8 Claims, 3 Drawing Figures

ACTH/Endorphin Precursor mRNA

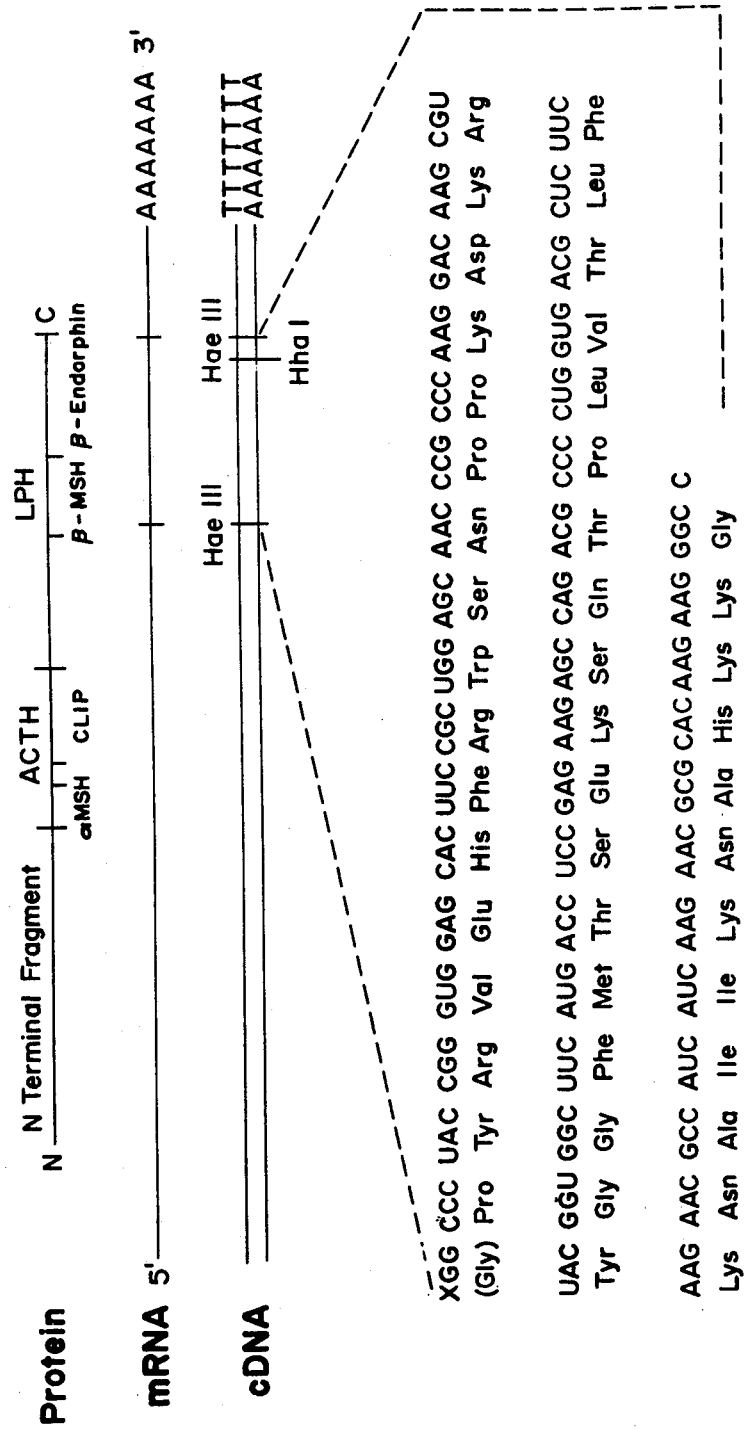

ADRENOCORTICOTROPIN-LIPOTROPIN PRECURSOR GENE

The Government has rights in this invention pursuant to Grants Nos. AM-19997 and CA-14026 awarded by the Department of Health, Education and Welfare.

BACKGROUND OF THE INVENTION

The invention herein provides means for the production of peptide hormones such as adrenocorticotropin (ACTH), endorphin, α- and β-melanocyte-stimulating hormone (α-MSH, β-MSH), β-lipotropin (β-LPH) and corticotropin-like intermedite lobe peptide (CLIP). These peptides have in common the fact that their synthesis in the body is coded by a single gene. Isolation of this gene, or portions thereof corresponding to one or more of the peptides for which it codes, enables the production of the desired peptides by in vitro or by microbiological systems. The invention is exemplified by the cloning of a deoxynucleotide sequence coding for endorphin.

Research results from several laboratories have established that the mammalian brain contains specific receptors which are the binding sites of opiate drugs. Recently, it has been shown that the normal brain contains certain peptides which specifically bind to the opiate receptors. These peptides are sometimes termed "endogenous opiates", in recognition of their role in normal brain physiology and of the similarity of their biological activity to that of such opium alkaloids as morphine. The name "endorphin" has been given to this class of peptides.

Various endorphins have been isolated and characterized. The largest is β-endorphin, having thirty-one amino acids in the following sequence: Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-His-Lys-Lys-Gly-Gln. (All peptide sequences herein begin with the N-terminal amino acid on the left and continue to the C-terminal amino acid on the right.) The α-, γ- and δ-endorphins are shorter subsequences of β-endorphin, having, respectively, the first sixteen, seventeen and twenty-seven amino acids, beginning at the amino-terminus of β-endorphin. All peptides in this series have in common the sequence: Tyr-Gly-Gly-Phe-Met, termed Met$^5$-enkephalin. Met$^5$-enkephalin has been separately isolated and shown to have morphine-like activity, which is naloxone-reversible. Met$^5$-enkephalin is the shortest sequence known to have opiod activity. Removal of the carboxy-terminal methionine results in complete loss of activity. A variant, Leu$^5$-enkephalin, is also active. The enkephalin moiety is considered to be the primary functional grouping conferring opioid activity on the endorphin molecule, while the effect of additional C-terminal amino acids primarily affects the rate of transport and duration of action of the peptide. For a general review, see Guillemin, R., *Science* 202, 390 (1978).

The β-endorphin amino acid sequence is included within a larger peptide, β-lipotropin (β-LPH), which lacks opiod activity, and has been previously isolated and characterized (Li, C.H. and Chung, D., *Proc.Nat. Acad. Sci USA* 73, 1145 (1976). ACTH is well known as a hormone which regulates the activity of the adrenal cortex. The subsequence of ACTH, termed, CLIP, comprising amino acids 15-39 of ACTH, has been shown experimentally to affect memory retention. The melanocyte-stimulating hormones stimulate pigment formation in the skin. Studies on stressed animals have revealed that β-endorphin and adrenocorticotropin (ACTH) concentrations in blood plasma increase at comparable rates following application of stress. More recently it was shown that both ACTH and β-LPH (containing the β-endorphin sequence), as well as α- and β-melanocyte-stimulating hormone (MSH) and a sequence of unknown function are initially synthesized as a single precursor protein having a molecular weight of approximately 28,500. (Roberts, J. L. and Herbert, E., *Proc.Nat.Acad.Sci USA* 74, 4826 (1977) (hereinafter cited as Roberts, J. L., et al., no. 1); Roberts, J. L. and Herbert, E., *Proc.Nat.Acad.Sci USA* 74, 5300 (1977) (hereinafter cited as Roberts, J. L., et al., no.2); Mains, et al., *Proc.Nat.Acad.Sci USA* 74, 3014 (1977)). The relative positions of the sequences of these peptides in the precursor peptide, hereinafter termed the ACTH/LPH precursor, are shown in FIG. 1.

The ACTH/LPH precursor is a central factor in normal physiological homeostasis. Normal maintenance functions are regulated by the peptide hormones comprising its amino acid sequence, and these hormones contribute to the normal sense of well-being of a healthy individual. The emerging picture also casts the ACTH/LPH precursor protein in the role of a "stress package" comprising segments capable of regulating behavioral, emotional and physiological responses to stress, selectively or in combination, depending upon the specific manner in which the precursor is ultimately cleaved. The ability to make adequate quantities of the entire precursor or its individual components is highly desirable for the therapy of stress-related diseases, for treatment of pain and for the management of psychosomatic illness.

It is clear from previous work that ACTH and endorphins exist only in very small amounts. Although they can be isolated from slaughterhouse material, the amounts are so minute that the purified material would be prohibitively expensive for therapeutic use. Similarly their length renders chemical synthesis excessively costly, using conventional methods. On the other hand, the use of recombinant DNA technology will enable the prctical production of ACTH and endorphins in sufficient quantity and at acceptable cost.

Developments in recombinant DNA technology have made it possible to isolate specific genes or portions thereof from higher organisms, such as man and other mammals, and to transfer the genes or fragments to a microorganism species, such as bacteria or yeast. The transferred gene is replicated and propagated as the transformed microorganism replicates. As a result, the transformed microorganism may become endowed with the capacity to make whatever protein the gene or fragment encodes, whether it be an enzyme, a hormone, an antigen or an antibody, or a portion thereof. The microorganism passes on this capability to its progeny, so that in effect, the transfer has resulted in a new strain, having the described capability. See, for example, Ullrich, A. et al., *Science* 196, 1313 (1977), and Seeburg, P. H., et al., *Nature* 270, 486 (1977). A basic fact underlying the application of this technology for practical purposes is that DNA of all living organisms, from microbes to man, is chemically similar, being composed of the same four nucleotides. The significant differences lie in the sequences of these nucleotides in the polymeric DNA molecule. The nucleotide sequences are used to specify the amino acid sequences of proteins that comprise the organism. Although most of the proteins of different organisms differ from each other, the coding relationship between nucleotide sequence and amino acid sequence is fundamentally the same for all organisms. For example, the same nucleotide sequence which codes for the amino acid sequence of ACTH in human pituitary cells, will, when transferred to a microorganism, be recognized as coding for the same amino acid sequence.

Abbreviations used herein are given in Table 1.

TABLE 1

| | | |
|---|---|---|
| DNA- | deoxyribonucleic acid | A-Adenine |
| RNA- | ribonucleic acid | T-Thymine |
| cDNA- | complementary DNA | G-Guanine |
| | (enzymatically synthesized | C-Cytosine |
| | from an mRNA sequence) | U-Uracil |
| mRNA- | messenger RNA | ATP-adenosine triphosphate |
| dATP- | deoxyadenosine triphosphate | TTP-thymidine triphosphate |
| dGTP- | deoxyguanosine triphosphate | |
| dCTP- | deoxycytidine triphosphate | |

The coding relationships between nucleotide sequence in DNA and amino acid sequence in protein are collectively known as the genetic code, shown in Table 2.

TABLE 2

Genetic Code

| | | | |
|---|---|---|---|
| Phenylalanine(Phe) | TTK | Histidine(His) | CAK |
| Leucine(Leu) | XTY | Glutamine(Gln) | CAJ |
| Isoleucine(Ile) | ATM | Asparagine(Asn) | AAK |
| Methionine(Met) | ATG | Lysine(Lys) | AAJ |
| Valine(Val) | GTL | Aspartic acid(Asp) | GAK |
| Serine(Ser) | QRS | Glutamic acid(Glu) | GAJ |
| Proline(Pro) | CCL | Cysteine(Cys) | TGK |
| Threonine(Thr) | ACL | Tryptophan(Try) | TGG |
| Alanine(Ala) | GCL | Arginine(Arg) | WGZ |
| Tyrosine(Tyr) | TAK | Glycine(Gly) | GGL |
| Termination signal | TAJ | | |
| Termination signal | TGA | | |

Key: Each 3-letter triplet represents a trinucleotide of mRNA, having a 5' end on the left and a 3' end on the right. The letters stand for the purine or pyrimidine bases forming the nucleotide sequence.

| | |
|---|---|
| A = adenine | J = A or G |
| G = guanine | K = T or C |
| C = cytosine | L = A, T, C or G |
| T = thymine | M = A, C or T |
| X = T or C if Y is A or G | |
| X = C if Y is C or T | |
| Y = A, G, C or T if X is C | |
| Y = A or G if X is T | |
| W = C or A if Z is A or G | |
| W = C if Z is C or T | |
| Z = A, G, C or T if W is C | |
| Z = A or G if W is A | |
| QR = TC if S is A, G, C or T | |
| QR = AG if S is T or C | |
| S = A, G, C or T if QR is TC | |
| S = T or C if QR is AG | |

An important feature of the code, for present purposes, is the fact that each amino acid is specified by a trinucleotide sequence, also known as a nucleotide triplet. The phosphodiester bonds joining adjacent triplets are chemically indistinguishable from all other internucleotide bonds in DNA. Therefore the nucleotide sequence cannot be read to code for a unique amino acid sequence without additional information to determine the reading frame, which is the term used to denote the grouping of triplets used by the cell in decoding the genetic message.

Many recombinant DNA techniques employ two classes of compounds, transfer vectors and restriction enzymes, to be discussed in turn. A transfer vector is a DNA molecule which contains, inter alia, genetic information which insures its own replication when transferred to a host microorganism strain. Examples of transfer vectors commonly used in bacterial genetics are plasmids and the DNA of certain bacteriophages. Although plasmids have been used as the transfer vectors for the work described herein, it will be understood that other types of transfer vector may be employed. Plasmid is the term applied to any autonomously replicating DNA unit which might be found in a microbial cell, other than the genome of the host cell itself. A plasmid is not genetically linked to the chromosome of the host cell. Plasmid DNA's exist as doublestranded ring structures generally on the order of a few million daltons molecular weight, although some are greater than $10^8$ daltons in molecular weight. They usually represent only a small percent of the total DNA of the cell. Transfer vector DNA is usually separable from host cell DNA by virtue of the great difference in size between them. Transfer vectors carry genetic information enabling them to replicate within the host cell, in some cases independently of the rate of host cell division. Some plasmids have the property that their replication rate can be controlled by the investigator by variations in the growth conditions. Plasmid DNA exists as a closed ring. However, by appropriate techniques, the ring may be opened, a fragment of heterologous DNA inserted, and the ring reclosed, forming an enlarged molecule comprising the inserted DNA segment. Bacteriophage DNA may carry a segment of heterologous DNA inserted in place of certain nonessential phage genes. Either way, the transfer vector serves as a carrier or vector for an inserted fragment of heterologous DNA.

Transfer is accomplished by a process known as transformation. During transformation, bacterial cells mixed with plasmid DNA incorporate entire plasmid molecules into the cells. Although the mechanics of the process remain obscure, it is possible to maximize the proportion of bacterial cells capable of taking up plasmid DNA and hence of being transformed, by certain empirically determined treatments. Once a cell has incorporated a plasmid, the latter is replicated within the cell and the plasmid replicas are distributed to the daughter cells when the cell divides. Any genetic information contained in the nucleotide sequence of the plasmid DNA can, in principle, be expressed in the host cell. Typically, a transformed host cell is recognized by its acquisition of traits carried on the plasmid, such as resistance to certain antibiotics. Different plasmids are recognizable by the different capabilities or combination of capabilities which they confer upon the host cell containing them. Any given plasmid may be made in quantity by growing a pure culture of cells containing the plasmid and isolating the plasmid DNA therefrom.

Restriction endonucleases are hydrolytic enzymes capable of catalyzing site-specific cleavage of DNA molecules. The locus of restriction endonuclease action is determined by the existence of a specific nucleotide sequence. Such a sequence is termed the recognition site for the restriction endonuclease. Restriction endonucleases from a variety of sources have been isolated and characterized in terms of the nucleotide sequence of their recognition sites. Some restriction endonucleases hydrolyze the phosphodiester bonds on both strands at the same point, producing blunt ends. Others catalyze hydrolysis of bonds separated by a few nucleotides from each other, producing free single stranded regions at each end of the cleaved molecule. Such single stranded ends are self-complementary, hence cohesive, and may be used to rejoin the hydrolyzed DNA. Since any DNA susceptible of cleavage by such an enzyme must contain the same recognition site, the same cohesive ends will be produced, so that it is possible to join heterologous sequences of DNA which have been treated with restriction endonuclease to other sequences similarly treated. See Roberts, R. J., *Crit.Rev.Biochem.* 4, 123 (1976). Restriction sites are relatively rare, however the general utility of restriction endonucleases has been greatly amplified by the chemical synthesis of double stranded oligonucleotides bearing the restriction site sequence. Therefore virtually any segment of DNA can be coupled to any other segment simply by attaching the appropriate restriction oligonucleotide to the ends of the molecule, and subjecting the product to the hydrolytic action of the appropriate restriction endonuclease, thereby producing the requisite cohesive ends. See Heyneker, H. L., et al., *Nature* 263, 748 (1976) and Scheller, R. H., et al., *Science* 196, 177 (1977). An important feature of the distribution of restriction endonuclease recognition sites is the fact that they are randomly distributed with respect to reading frame. Consequently, cleavage by restriction endonuclease may occur between adjacent codons or it may occur within a codon.

More general methods for DNA cleavage or for end sequence modification are available. A variety of nonspecific endonucleases may be used to cleave DNA randomly, as discussed infra. End sequences may be modified by addition of random sequences of dA+dT or dG+dC, to create restriction sites without the need for specific linker sequences.

The term "expression" is used in recognition of the fact that an organism seldom if ever makes use of all its genetically endowed capabilities at any given time. Even in relatively simple organisms such as bacteria, many proteins which the cell is capable of synthesizing are not synthesized, although they may be synthesized under appropriate environmental conditions. When the protein product, coded by a given gene, is synthesized by the organism, the gene is said to be expressed. If the protein product is not made, the gene is not expressed. Normally, the expression of genes in *E. coli* is regulated as described generally, infra, in such manner that proteins whose function is not useful in a given environment are not synthesized and metabolic energy is conserved.

The means by which gene expression is controlled in *E. coli* is well understood, as the result of extensive studies over the past twenty years. See, generally, Hayes, W., *The Genetics of Bacteria And Their Viruses*, 2d edition, John Wiley and Sons, Inc., New York (1968), and Watson, J. D., *The Molecular Biology of the Gene*, 3d edition, Benjamin, Menlo Park, California (1976). These studies have revealed that several genes, usually those coding for proteins carrying out related functions in the cell, are found clustered together in continuous sequence. The cluster is called an operon. All genes in the operon are transcribed in the same direction, beginning with the codons coding for the N-terminal amino acid of the first protein in the sequence and continuing through to the C-terminal end of the last protein in the operon. At the beginning of the operon, proximal to the N-terminal amino acid codon, there exists a region of the DNA, termed the control region, which includes a variety of controlling elements including the operator, promoter and sequences for the ribosomal binding sites. The function of these sites is to permit the expression of those genes under their control to be responsive to the needs of the organism. For example, those genes coding for enzymes required exclusively for utilization of lactose are not expressed unless lactose or an analog thereof is actually present in the medium. The control region functions that must be present for expression to occur are the initiation of transcription and the initiation of translation. Expression of the first gene in the sequence is initiated by the initiation of transcription and translation at the position coding for the N-terminal amino acid of the first protein of the operon. The expression of each gene downstream from that point is also initiated in turn, at least until a termination signal or another operon is encountered with its own control region, keyed to respond to a different set of environmental cues. While there are many variations in detail on this general scheme, the important fact is that, to be expressed in a procaryote such as *E. coli*, a gene must be properly located with respect to a control region having initiator of transcription and initiator of translation functions.

It has been demonstrated that genes not normally part of a given operon can be inserted within the operon and controlled by it. The classic demonstration was made by Jacob, F., et al., *J.Mol.Biol.* 13, 704 (1965). In that experiment, genes coding for enzymes involved in a purine biosynthesis pathway are transferred to a region controlled by the lactose operon. The expression of the purine biosynthetic enzyme was then observed to be repressed in the absence of lactose or a lactose analog, and was rendered unresponsive to the environmental cues normally regulating its expression.

In addition to the operator region regulating the initiation of transcription of genes downstream from it, there are known to exist condons which function as stop signals, indicating the C-terminal end of a given protein. See Table 2. Such codons are known as termination signals and also nonsense codons, since they do not normally code for any amino acid. Deletion of a termination signal between structural genes of an operon creates a fused gene which could result in the synthesis of a chimeric protein consisting of two amino acid sequences coded by adjacent genes, joined by a peptide bond. That such chimeric proteins are synthesized when genes are fused was demonstrated by Benzer, S., and Champe, S. P., *Proc.Nat.Acad.Sci USA* 48, 14 (1962).

Once a given gene has been isolated, purified and inserted in a transfer vector, the over-all result of which is termed the cloning of the gene, its availablility in substantial quantity is assured. The cloned gene is transfered to a suitable microorganism, wherein the gene replicates as the microorganism proliferates and from which the gene may be reisolated by conventional means. Thus is provided a continuously renewable source of the gene for further manipulations, modifications and transfers to other vectors or other loci within the same vector.

Expression is obtained by transferring the cloned gene, in proper orientation and reading frame, into a control region such that read-through from the procaryotic gene results in synthesis of a chimeric protein comprising the amino acid sequence coded by the cloned gene. A variety of specific protein cleavage techniques may be used to cleave the chimeric protein at a desired point so as to release the desired amino acid sequence, which may then be purified by conventional means. Techniques for constructing an expression transfer vector having the cloned gene in proper juxtaposition with a control region are described in Polisky, B., et al., *Proc.Nat.Acad.Sci USA* 73, 3900 (1976); Itakura, K., et al., *Science* 198, 1056 (1977); Villa-Komaroff, L., et al., *Proc.Nat.Acad.Sci USA* 75, 3727 (1978); Mercereau-Puijalon, O., et al, *Nature* 275, 505 (1978); Chang, A. C. Y., et al, *Nature* 275, 617 (1978), and in U.S. application Ser. No. 933,035 by Rutter, et al., said application incorporated herein by reference as though set forth in full.

In summary, the process whereby a mammalian protein, such as ACTH or endorphin, is produced with the aid of recombinant DNA technology first requires the cloning of the mammalian gene. Once cloned, the gene may be produced in quantity, further modified by chemical or enzymic means and transferred to an expression plasmid. The cloned gene is also useful for isolating related genes, or, where a fragment is cloned, for isolating the entire gene, by using the cloned gene as a hybridization probe. Further, the cloned gene is useful in proving by hybridization, the identity or homology of independent isolates of the same or related genes. Because of the nature of the genetic code, the cloned gene, when translated in the proper reading frame, will direct the production only of the amino acid sequence for which it codes and no other.

In the case of the cloned endorphin gene, its transposition to an expression transfer vector will permit the synthesis of endorphin by a host microorganism transformed with the vector carrying the cloned gene. Growth of the transferred host will result in synthesis of endorphin, under appropriate environmental conditions. Endorphin is useful as a morphine agonist and as an analgesic. There is a substantial degree of species cross-reactivity in the endorphins, with any interspecific differences being confined to that portion of the molecule outside the essential enkephalin sequence. The β-endorphin of mouse is identical to that of sheep in amino acid sequence and differs from that of man only at position 28, where there is a His residue in mouse and a Tyr residue in the human sequence. The enkephalin moiety bearing the primary functional modality of mouse endorphin is the same as for man. Therefore, mouse endorphin differing only by a single amino acid substitution at position 28 from the human peptide will have essentially the same activity in man as the human peptide itself, perhaps differing slightly in such parameters as duration of action or dose response. Other sequence variants, either naturally-occurring, or man made, may be found, which can confer tissue specificity on the analgesic action of endorphins, thereby permitting relief of localized pain.

Similar considerations apply to other portions of the ACTH/LPH gene. ACTH, for example, is useful to regulate adrenal cortex output, and to prevent depression of adrenal cortex output during corticosteroid therapy. ACTH is widely used in a test for diagnostic evaluation of the hypophysispituitary axis, for example in the detection of Addison's disease. Use of ACTH is sometimes advocated where excessive inflammatory or immunological activity contributes to the symptoms, as in ulcerative colitis. Inter-species cross-reactivity is also observed with ACTH, so that non-human ACTH is useful in treatment of human disease as well as in veterinary medicine. The α- and β-MSH moieties are active in the physiological tanning process. Administration of these hormones can produce darkening of the skin in a manner essentially indistinguishable from natural tanning. Interspecies cross-reactivity is observed with these hormones.

The foregoing considerations apply as well to the cloned gene for the entire ACTH/LPH precursor.

SUMMARY OF THE INVENTION

In the present invention, a technique suitable for cloning a cDNA having a base sequence coding for the ACTH/LPH precursor is disclosed. The invention is exemplified by the cloning of a cDNA fragment comprising a base sequence coding for the endorphin region. The fragment, hereinafter termed the endorphin gene cDNA sequence, was obtained from cultured mouse pituitary tumor cells known to produce the ACTH/LPH precursor protein.

Messenger RNA was isolated from the cells and purified by chromatography and sedimentation. Active fractions were identified by their ability to direct the synthesis of protein immunochemically reactive with antisera specific to ACTH or to β-endorphin in a cell-free protein synthesizing system.

DNA complementary to the isolated messenger RNA (cDNA) was synthesized, using reverse transcriptase. From the heterogeneous-length double-stranded cDNA product, homogeneous length fragments were generated by restriction endonuclease treatment. The choice of the particular restriction endonuclease used determined the size distribution of the fragments and also determined which fragments contained desired sequences. For cloning the endorphin gene cDNA sequence, a fragment about 140 base pairs in length was chosen, produced by the enzyme HaeIII. Fragments generated by the enzyme treatment were separated according to length.

The purified fragments were recombined with a suitable transfer vector, using currently available techniques. The endorphin gene cDNA sequence was transferred to the HindIII site in plasmid pBR-322 with the aid of specific HindIII linker oligonucleotides attached at either end, using the enzyme DNA ligase. Similar techniques are suitable for recombining the purified fragment with other transfer vectors, including vectors specifically designed to permit expression of the recombinant fragment.

Replication and propagation of the recombinant transfer vector containing the purified cDNA fragment was accomplished by transforming a host microorganism with the recombinant vector. Replication of the recombinant vector occurred in the normal course of growth and cell division of the host. The cloned gene, amplified in number to the desired extent, was reisolated from cell extracts of the host microorganism, using currently available techniques. The cloned endorphin gene was isolated in quantity after multiple rounds of replication, and was characterized by determining its nucleotide sequence. The cloned endorphin gene cDNA sequence was shown to code for 17 amino acids preceding the amino terminus and for 30 amino acids of the sequence of β-endorphin.

DETAILED DESCRIPTION OF THE INVENTION

Figure 1:
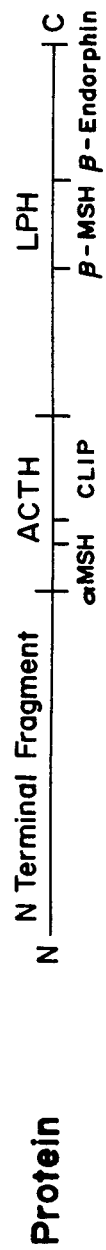

ACTH is synthesized by the anterior lobe of the pituitary gland. Endorphin is found in relatively high concentrations in extracts of posterior pituitary-hypothalamic tissue. However, the ACTH/LPH precursor protein is found in equivalent proportions in both lobes. Therefore, although the precursor is processed differently in the two lobes, as a practical matter cells from either or both should be a suitable source of precursor messenger RNA. Pituitary tumor cells, either obtained surgically or maintained in culture, are suitable source materials. See Roberts, J. L., et al., *Biochemistry* 17, 3609 (1978). Human pituitary tumor cells are obtainable from human patients by transphenoidal hypophysectomy. Alternatively, certain ectopic ACTH-producing tumors are known, notably the oat-cell carcinoma of the lung, which can be used as a source of ACTH/LPH precursor mRNA.

A convenient and presently preferred method for isolating and purifying the cDNA sequence coding for the ACTH/LPH precursor or portion thereof, is to first partially purify the messenger RNA coding for the precursor from cell extracts. Partially purified messenger RNA may be used as a template to construct complementary DNA (cDNA), using reverse transcriptase. Double-stranded cDNA may be directly recombined with a suitable transfer vector or subjected to restriction endonuclease cleavage and subsequent purification of discrete fragments, according to the technique described by Goodman, et al. in application Ser. No. 897,710, incorporated herein by reference as though set forth in full. Alternative to isolating messenger RNA, the DNA of the pituitary cells may be isolated and purified. However, mRNA isolation is presently preferred, firstly because the differentiation of eucaryotic cells provides a substantial prepurification, since only a fraction of the total genome is transcribed into mRNA. Secondly, the desired mRNA is frequently present as a substantial proportion of the total mRNA. Thirdly, the desired mRNA can be functionally identified, after fractionation, by its ability to direct synthesis of the desired protein in a cell-free protein synthesis system. Fourthly, the initial mRNA isolation and purification stages can be carried out without special containment requirements (See "Recombinant DNA Research Guidelines", 41 Fed. Reg. 27902–27943, July 7, 1976 and "Proposed Revised Guidelines", 43 Fed. Reg. 33042–33178, July 28, 1978). Fifthly, it is known that eucaryotic genes sometimes include non-coding intervening sequences, which, if included in the gene transferred to a host microorganism, might be incorrectly translated, after transcription into mRNA, such that a non-functional protein could be produced. Whether this situation obtains in the ACTH/LPH precursor gene, is presently unknown.

The isolation and purification of mRNA and the synthesis of cDNA therefrom are described in detail in Goodman, et al., supra, and by Ullrich, A., et al., *Science* 196, 1313 (1977). cDNA prepared from an mRNA template is frequently heterodisperse in molecular length, especially if the mRNA template is heterodisperse. However, homogeneous length molecules of a given sequence can be obtained essentially pure by treatment with one or more restriction endonucleases followed by fractionation, preferably by gel electrophoresis, according to molecular length, as described by Goodman, et al., supra. The choice of which restriction endonuclease to use is based upon knowledge of the nucleotide sequence specificity of each restriction enzyme and upon whatever nucleotide sequence information is known of the cDNA, or is inferrable from the amino acid sequence of the protein. In the case of the ACTH/LPH precursor, the endorphin region is conveniently bracketed by two HaeIII sites permitting the purification of a 144 base pair fragment containing the nucleotide sequence coding for endorphin. More precisely, the endorphin gene thus purified contains all but the —COOH terminal amino acid in the sequence of β-endorphin. The resulting protein will not be substantially affected functionally for the reasons presented, supra.

Similarly, an ACTH coding cDNA fragment could be purified. The same mRNA fraction known to contain the endorphin coding sequence also contained mRNA capable of directing the synthesis of protein reactive with antisera to ACTH. Other desired fragments may be purified in similar fashion.

Full length ACTH/LPH precursor cDNA may be purified directly from total cDNA or by religation of restriction fragments, as described by Goodman, et al., supra. Alternatively, purified cDNA fragments may be hybridized with full length cDNA in order to purify sequences of the latter having a region of substantial homology.

Once the desired gene cDNA sequence is purified, the techniques for insertion into a DNA transfer vector are straightforward. See Ullrich, A., et al., supra, Goodman, et al., supra and Rutter, et al., supra. Methods for modifying the end groups of transfer vector DNA and cDNA to be recombined are described by Rutter, et al., supra, Villa-Komaroff, et al., supra and by Scheller, et al., *Science* 196, 177 (1977).

The identity of a given cloned gene cDNA sequence can be ascertained in various ways. Frequently it will suffice to identify the cDNA sequence on the basis of a known restriction site located asymmetrically within it. For example, the 144 base pair endorphin sequence, liberated from the transfer vector by HindIII cleavage, can be identified by the fact that a HhaI site exists within it such that HhaI cleavage results in two fragments of 132 and 12 base pairs, respectively, identifiable by gel electrophoresis. An unequivocal proof of identity is provided by determining the nucleotide sequence of the cloned gene. Even a partial sequence, if extended over a reasonable distance, at least 30 base pairs, provides acceptable evidence of identity. Methods for sequence determination have been published by Maxam, A. M., et al., *Proc.Nat.Acad.Sci USA* 74, 560 (1977) and by Sanger, F., et al., *Proc.Nat.Acad.Sci USA* 74, 5463 (1977).

Adequate quantities of the cloned gene are readily available once the gene is recombined with a transfer vector and transferred to a suitable host microorganism. The transfer vector containing a cloned gene is readily purified from cultures of the host microorganism by currently available techniques. The cloned gene is separable from the transfer vector by restriction endonuclease cleavage followed by gel electrophoresis or other fractionation based on molecular size. See, e.g., Rutter, et al., supra.

The cloned gene is used to direct the synthesis of the peptide for which it codes in either an in vitro or in vivo system. In vitro protein synthesis directed by DNA has been demonstrated in a variety of systems, see, for example, Herrlich, P., et al., "DNA- and RNA-directed Synthesis In Vitro of Phage Enzymes" in *Methods in Enzymology* (L. Grossman and K. Moldave, eds.) vol. 30, p. 654, Academic Press, New York (1974).

In vivo synthesis of the peptide can occur when the cloned gene has been recombined with a transfer vector in such a way that the cloned gene is inserted into a gene of the host that is normally expressed in proper orientation and phase, such that a chimeric protein is produced having portions derived from the host gene and the cloned gene. There are numberous techniques for specifically cleaving the chimeric protein to generate the desired peptide, coded by the cloned gene. The choice will depend upon specifics of the chimeric sequence. Specific cleavage at methionine residues results from cyanogen bromide treatment. A methionine residue is readily incorporated into the chimeric protein just before the cloned sequence, by use of an appropriate linker oligonucleotide in the recombination step. See Itakura, et al., supra. Where a methionine residue exists within the desired peptide, other techniques must be used. Trypsin and chymotrypsin have well-characterized sequence specificities which can be exploited. For example, the enkephalin sequence will be generated by exhaustive tryptic digestion of a chimeric protein containing the peptide coded by the endorphin gene. Mild tryptic digestion is expected to yield the endorphin sequence. The cloned sequence could be modified to provide trypsin-sensitive sites at desired loci. Further, it is known, in the case of peptide hormones synthesized in precursor form, that hydrolytic enzymes exist, specifically active in removing the precursor sequence from the hormone (See, Blobel, G., et al., *Proc.Nat.Acad.Sci USA* 75, 361 (1978). Such enzymes could be exploited to yield ACTH, endorphin and other biologically active fragments from the ACTH/LPH precursor. Other techniques will be suggested to those skilled in the art.

Specific application of the above-described invention will be demonstrated by the following examples.

EXAMPLE 1

ACTH/LPH precursor cDNA

Mouse pituitary tumor cells of the AtT-20/D-16v line were obtained from Dr. Edward Herbert, University of Oregon and grown in culture as described by Roberts, J. L., et al., no. 1, supra. Extraction of mRNA was performed essentially as described by Godman, et al., supra, following homogenization in 4 M guanidinium thiocyanate and 2-mercaptoethanol, as described by Ullrich, A., et al., supra. The mRNA was purified essentially as described by Goodman, et al., supra, using chromatography on oligo dT-cellulose and sucrose gradient sedimentation. Fractions coding for ACTH/LPH precursor protein were identified by their ability to direct synthesis of protein reactive with antisera against ACTH and against $\beta$-endorphin (Roberts, J. L. no. 2, supra).

Figure 2:
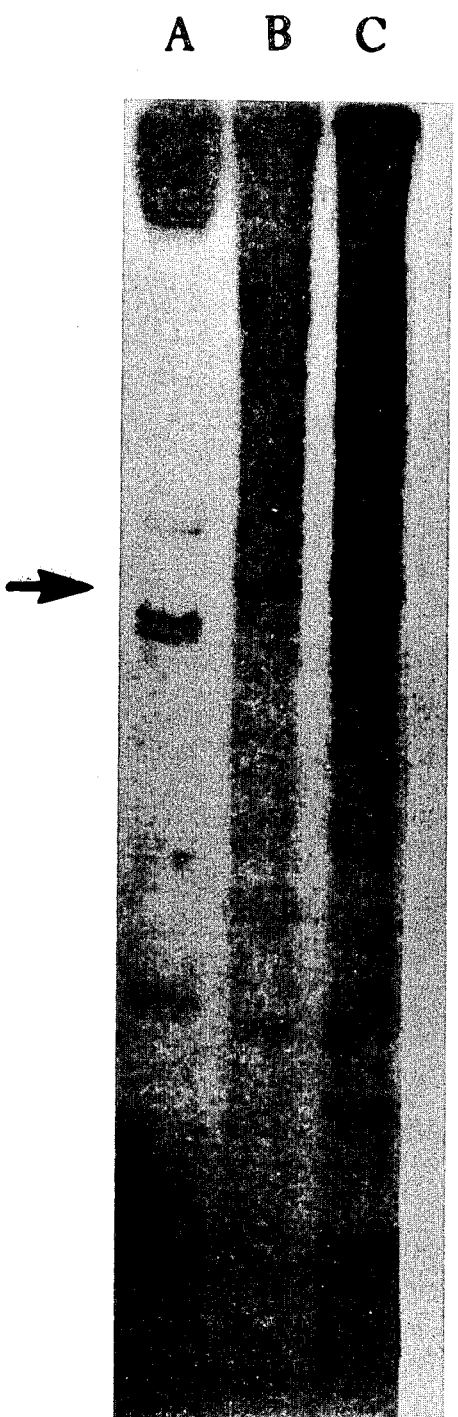

Synthesis of cDNA based on active mRNA fractions was carried out essentially as described by Goodman, et al., supra. Total cDNA prepared in this manner was heterodisperse. In order to purify a specific fragment, the double-stranded cDNA was cleaved with the restriction endonuclease HaeIII. All restriction enzymes described herein are commercially available from New England Biolabs, Beverly, Massachusetts. The reaction mixture was then phenol extracted, ethanol precipitated, redissolved and fractionated by gel electrophoresis, as described by Goodman, et al., supra. The resulting electrophoresis pattern is shown in FIG. 2. Column (a) shows the positions of known size markers obtained from HpaII treated bacteriophage fD DNA. Column (b) shows the pattern resulting from cleavage by HaeIII of cDNA from total mRNA prior to sucrose gradient sedimentation. Column (c) is the pattern resulting from cleavage by HaeIII of cDNA from the highly enriched ACTH/LPH mRNA fraction after sucrose gradient sedimentation. The arrow indicates the position of a cDNA fragment of approximately 140 base pairs length. This band was eluted separately from the gel and used for further studies.

EXAMPLE 2

Construction of a recombinant plasmid containing the endorphin gene cDNA sequence The techniques used herein were essentially as described by Goodman, et al., supra, and by Ullrich, et al., supra. The approximately 140 base pair fragment was inserted into the HindIII site of plasmid pBR-322. Insertion was facilitated by the addition of octanucleotide HindIII linkers at both ends of the fragment, using DNA ligase. Self-ligation of HindIII-treated pBR-322 was prevented by pretreatment with alkaline phosphatase. Cells of *E. coli* $\chi$1776 were transformed by the product resulting from mixing HindIII- and alkaline phosphatase-treated pBR-322 and the 140 base-pair fragment, treated as described, with DNA ligase. Transformants having pBR-322 with an insertion at the HindIII site were identified by resistance to ampicillin and sensitivity to 20 $\mu$g/ml tetracycline. Single colonies were then picked, grown in culture and the plasmid DNA was reisolated from each. After treatment with HindIII endonuclease, the DNA was fractionated by gel electrophoresis. The endorphin gene cDNA sequence was expected to have a HhaI site asymmetrically located so as to yield fragments of approximately 132 and 12 base pairs. The existence of the HhaI site and its location was previously determined by analysis of AtT-20 cDNA HaeIII fragments.

On the basis of the foregoing experiment, the approximately 140 base pair fragment, designated ME-150, was identified as the cloned endorphin gene cDNA sequence.

A novel plasmid, designated pBR-322/ME-150, was produced according to the foregoing procedure. A novel microorganism, *E. coli* $\chi$1776 transformed by pBR-322/ME-150, was also produced. The organism is designated *E. coli* $\chi$1776-ME-150. The novel microorganism and the novel plasmid were placed on deposit in the American Type Culture Collection on Dec. 21, 1978. The ATCC accession number for *E. coli* $\chi$1776/ME150 is 31477. The accession number for plasmid pBR322/ME150 is 40007.

EXAMPLE 3

Nucleotide sequence determination

The nucleotide sequence of ME-150 was determined by the method of Maxam, A. M., et al., supra. Results are shown in FIG. 3. The nucleotide sequence codes for the amino acid sequence are shown in Table 1.

Table 1

Pro-Tyr-Arg-Val-Glu-His-Phe-Arg-Trp-Ser-Asn-Pro-
Pro-Lys-Asp-Lys-Arg-Tyr-Gly-Gly-Phe-Met-Thr-
Ser-Glu-Lys-Ser-Glu-Thr-Pro-Leu-Val-Thr-Leu-

Phe-Lys-Asn-Ala-Ile-Ile-Lys-Asn-Ala-His-Lys-Lys-Gly

The cloned cDNA nucleotide sequence, expressed as mRNA in FIG. 3, is shown in Table 2.

Table 2

5'-GG CCC TAC CGG GTG GAG CAC TTC CGC TGG AGC AAC CCG CCC AAG GAC AAG CGT TAC GGT GGC TTC ATG ACC TCC GAG AAG AGC CAG ACG CCC CTG GTG ACG CTC TTC AAG AAC GCC ATC ATC AAG AAC GCG CAC AAG AAG GGC C-3'

It can be seen that the cloned gene cDNA sequence comprises 143 base pairs, of which 2–52 correspond to amino acids 44–60 of mouse β-LPH and 53–142 correspond to amino acids 1–30 of mouse endorphin. The amino acid sequences correspond to the known sequence for sheep except in positions 44–47 and 53–54. Within the endorphin region itself, the mouse sequence is identical to sheep, and essentially similar to the human sequence, differing only at position 28 a Tyr residue exists in the human sequence.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A recombinant DNA plasmid or bacteriophage transfer vector comprising a cDNA sequence comprising the endorphin gene cDNA sequence.

2. The transfer vector of claim 1 wherein the cDNA sequence comprises cDNA coding for the amino acid sequence: Pro-Tyr-Arg-Val-Glu-His-Phe-Arg-Trp-Ser-Asn-Pro-Pro-Lys-Asp-Lys-Arg-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-His-Lys-Lys-Gly.

3. The transfer vector of claim 1 comprising the cDNA sequence: 5'-GG CCC TAC CGG GTG GAG CAC TTC CGC TGG AGC AAC CCG CCC AAG GAC AAG CGT TAC GGT GGC TTC ATG ACC TCC GAG AAG AGC GAG ACG CCC CTG GTG ACG CTC TTC AAG AAC GCC ATC ATC AAG AAC CGC CAC AAG AAG GGC C-3'.

4. A microorganism transformed by the transfer vector of claim 1.

5. A microorganism transformed by the transfer vector of claim 2.

6. The plasmid pBR-322/ME-150.

7. Bacteria transformed by the plasmid of claim 6.

8. The microorganism *E. coli* χ1776-ME-150.

* * * * *